US012282011B2

(12) United States Patent
Notari et al.

(10) Patent No.: US 12,282,011 B2
(45) Date of Patent: Apr. 22, 2025

(54) METHOD FOR THE ASSESSMENT OF THE DISPERSING CAPACITY OF NEW OR USED LUBRICATING COMPOSITIONS AND OF ADDITIVES FOR LUBRICATING COMPOSITIONS

(71) Applicant: ENI S.P.A., Rome (IT)

(72) Inventors: Marcello Notari, San Donato Milanese (IT); Riccardo Rausa, San Donato Milanese (IT); Giulio Assanelli, San Donato Milanese (IT); Giovanni Ferraro, Florence (IT); Emiliano Fratini, Sesto Fiorentino (IT); Piero Baglioni, Fiesole (IT)

(73) Assignee: ENI S.P.A., Rome (IT)

( * ) Notice: Subject to any disclaimer, the term of this patent is extended or adjusted under 35 U.S.C. 154(b) by 280 days.

(21) Appl. No.: 17/917,758

(22) PCT Filed: Apr. 7, 2021

(86) PCT No.: PCT/IB2021/052891
§ 371 (c)(1),
(2) Date: Oct. 7, 2022

(87) PCT Pub. No.: WO2021/205360
PCT Pub. Date: Oct. 14, 2021

(65) Prior Publication Data
US 2023/0168237 A1 Jun. 1, 2023

(30) Foreign Application Priority Data
Apr. 7, 2020 (IT) .................... 102020000007351

(51) Int. Cl.
*G01N 33/28* (2006.01)
*G01N 15/0205* (2024.01)

(52) U.S. Cl.
CPC ..... *G01N 33/2888* (2013.01); *G01N 15/0205* (2013.01)

(58) Field of Classification Search
CPC ...................... G01N 15/0205; G01N 33/2888
See application file for complete search history.

(56) References Cited

U.S. PATENT DOCUMENTS

| 4,936,016 A | 6/1990 | Simpson |
| 5,313,824 A * | 5/1994 | Herguth ............. G01N 33/2888 |
| | | 356/70 |

(Continued)

OTHER PUBLICATIONS

Muggli et al. "An Experimental Approach to Assess the Dispersion of Shale in Fracturing Fluids," Society of Petroleum Engineers SPE-197044, pp. 245-254 (Year: 2020).*

(Continued)

*Primary Examiner* — John Fitzgerald
(74) *Attorney, Agent, or Firm* — Ruggiero McAllister & McMahon LLC (57) ABSTRACT

A method for the assessment of the dispersing capacity of new and used lubricating compositions, in particular for internal combustion engines, and of additives for lubricating compositions, includes the steps of: providing a homogeneous dispersion of at least one carbonaceous particulate in a composition to be tested, consisting of a lubricating composition or a fraction or component thereof, acquiring at least one micrographic image of a sample of said homogeneous dispersion, deposited on an observation support, and calculating the lacunarity of the acquired image as a parameter representative of the degree of dispersion of the particulate in the composition.

20 Claims, 7 Drawing Sheets

(56) References Cited

U.S. PATENT DOCUMENTS

| | | | | |
|---|---|---|---|---|
| 5,817,928 | A * | 10/1998 | Garvey, III | G01N 33/2888 |
| | | | | 324/698 |
| 6,417,920 | B1 * | 7/2002 | Shimaoka | G01N 15/0205 |
| | | | | 356/336 |
| 6,473,178 | B2 * | 10/2002 | Shimaoka | G01N 15/0205 |
| | | | | 356/336 |
| 7,380,441 | B2 * | 6/2008 | Wollenberg | G01N 33/2888 |
| | | | | 73/61.41 |
| 8,208,698 | B2 * | 6/2012 | Bogdan | G06T 7/0012 |
| | | | | 382/128 |
| 9,664,627 | B2 * | 5/2017 | Horstmeyer | G01N 21/94 |
| 10,126,220 | B2 * | 11/2018 | Larson | G01N 9/10 |
| 10,519,800 | B2 * | 12/2019 | Jean | F01D 21/003 |
| 10,539,547 | B2 * | 1/2020 | Pigeon | G06T 7/001 |
| 2012/0224753 | A1 * | 9/2012 | Bogdan | G06T 7/42 |
| | | | | 382/128 |
| 2015/0362421 | A1 | 12/2015 | Lewis et al. | |
| 2022/0074840 | A1 * | 3/2022 | Monden | G01N 15/0211 |

OTHER PUBLICATIONS

International Search Report and Written Opinion for corresponding International (PCT) application No. PCT/ B2021/052891, 13 pages, dated Jul. 1, 2021.

Pennella et al "Numerical and Experimental Characterization of a Novel Modular Passive Micromixer", Biomedical Devices, vol. 14, No. 5, Jun. 19, 2012 pp. 849-862; Springer Science+Business Media LLC.

* cited by examiner

METHOD FOR THE ASSESSMENT OF THE DISPERSING CAPACITY OF NEW OR USED LUBRICATING COMPOSITIONS AND OF ADDITIVES FOR LUBRICATING COMPOSITIONS

CROSS-REFERENCE TO RELATED APPLICATIONS

This Patent Application is a national stage application, filed under 35 U.S.C. § 371, of International Application No. PCT/IB2021/052891 filed on Apr. 7, 2021 that claims priority from Italian Patent Application No. 102020000007351 filed on Apr. 7, 2020, the entire disclosure of each which is incorporated herein by reference.

BACKGROUND OF THE DISCLOSURE

(1) Field of the Disclosure

The present invention relates to a method for the assessment of the dispersing capacity of new and used lubricating compositions (in particular for internal combustion engines) and of additives for lubricating compositions.

(2) Description of Related Art

As known, lubricants (intended as lubricating compositions) for internal combustion engines are normally subject to thermal and oxidative degradation. One of the most important properties of a lubricant is therefore its capacity of dispersing, by holding in suspension, the products deriving from thermal and oxidative degradation.

Oxidation, which is the main cause of lubricant degradation, is the result of the interaction of the lubricating components with oxygen and fuel combustion by-products. The components of the lubricant, at engine operating temperatures, are involved in a complex series of radical reactions that originate highly polar products. These oxidation products, being insoluble in the lubricant, have a tendency to separate, aggregate and deposit on metal surfaces, for example in the stationary areas of the engine, leading to an increase in the viscosity of the lubricant, obstruction of the distribution ducts, gelling of the lubricant at low temperature with strong reduction of its pumpability, and wear phenomena.

To reduce the aforementioned phenomena, lubricants contain dispersing additives, which control the state of aggregation of the polar insoluble carbonaceous compounds (known as "soot" in diesel engines and "sludge" in gasoline engines), dispersing them in the lubricating composition and preventing the precipitation thereof.

Also as a result of the continuous evolution of the laws governing emissions from internal combustion engines, constant technological innovation is also necessary in the lubricants sector, whose performance is subject to increasingly stringent specifications.

The development of new lubricants requires a qualification step which, necessarily taking place through specific engine tests, is economically very expensive.

In fact, the methods available for assessing a given lubricating composition and in particular the dispersing properties thereof consist of mainly engine tests, which are representative of the real situation in which the lubricants work. The engine tests are generally part of performance specifications for the qualification of lubricants for petrol and diesel engines, which are issued by Manufacturers and by International Bodies, such as ACEA (Association des Constructeurs Européens de l'Automobile), API (American Petroleum Institute), JASO (Japanese Automobile Standards Organization) and ILSAC (International Lubricant Standardization and Approval Committee).

The engine testing methods are developed and issued by bodies, the main ones among them being CEC (Coordinating European Council) and ASTM (American Society for Testing and Materials).

In general, various parameters can be determined in an engine test for the assessment of the dispersing capacity, among which the most common ones are the variation of the viscosity of the lubricant and the amount of particulate present.

It is well known in the literature that an increase in the amount of particulate is generally connected to an increase in the viscosity of the system, as reported for example in the articles: G. Ferraro, E. Fratini, R. Rausa, P. Baglioni, "Journal of Colloid and Interface Science" 512 (2018), 291-299; K. Selby, "Rheology of Soot Thickened Diesel Engine Oils", SAE Technical Paper 981369, 1998.

Examples of engine tests for the assessment of the dispersing capacity of particulate by a lubricant in diesel engines for cars are as follows.

Test DV4TD—CEC L-93-04

This engine test (now no longer in use but still cited in the qualifications of lubricants on the market) aims to assess the effect of the combustion particulate on the increase in the viscosity of the lubricant and on the cleanliness of the engine pistons. The test procedure simulates the high-speed road service of a car equipped with an inline four-cylinder Peugeot DV4TD/L4 common rail diesel engine. Pistons and rings are classified at the end of the test for the deposits and the adherence of the rings. The procedure includes the assessment every 24 hours of test of the viscosity at 100° C., of the particulate content and of the iron content in the used oil.

At the end of the test, the increase in absolute viscosity is reported by interpolating the obtained values with that corresponding to a particulate content of 6% m/m.

Test DV6—CEC L-106-04

The method allows to assess the capacity of the lubricant of dispersing combustion particulates accumulated during intense engine operation. The test cycle consists of two main steps, one at 3600 rpm under full load and the other at 1750 rpm with EGR. The duration of one cycle is 1 hour, with both main steps interspersed with short steps at 1000 rpm. The cycle is repeated for 120 hours. The engine used is a PSA 1.6 L DV6 common rail diesel engine with direct injection and intercooler. The performance of the lubricant is assessed by determining the viscosity increase at 100° C. which occurs at a particulate concentration of 5.5% by weight. The cleanliness of the pistons is also assessed.

Examples of engine tests for the assessment of the dispersing capacity of particulate by the lubricant in Heavy Duty diesel engines are as follows.

Tests Mack T-8, T-8A and T-8E (ASTM D5967)

These tests were developed to assess the performance in terms of viscosity increase, linked to the formation of particulate, of lubricants in turbocharged four-stroke diesel engines with intercooler. The tests use a Mack E7-350 direct injection diesel engine, with 6 inline cylinders and 4 valves per cylinder. The test is conducted at 1800 rpm.

The T-8A test has a duration of 150 hours and is used for the qualification of lubricants according to the API CF-4 specification.

The T-8 test has a duration of 250 hours and is used for the qualification of lubricants according to the API CG-4 specification.

The T-8E test has a duration of 300 hours and is used for the qualifications of lubricants according to API CH-4, API CI-4, ACEA E4, E6 and E7 specifications.

Test Mack T-11 (ASTM D7156)

This test was developed to assess the performance in terms of viscosity increase, linked to the formation of particulate, of lubricants in turbocharged, four-stroke diesel engines with intercooler and equipped with EGR.

The test envisages the use of a 4-stroke Mack E-TECH V-MAC III diesel engine with exhaust gas recirculation (EGR). The test lasts 252 hours under constant load conditions. The test is used for API CI-4 Plus, CJ-4, CK-4 and ACEA E9 qualifications.

In general, the engine assessments have the merit, compared to laboratory tests (which will be shown below), of reproducing the behaviour of the lubricant in real operating conditions on the engine. On the other hand, all these methods and in particular the engine tests for Heavy Duty lubricants (HDDO: Heavy Duty Diesel Oil) are very expensive and require large amounts of lubricant, therefore it is very expensive to use them for the preliminary assessment of several candidate compositions.

On a laboratory scale, however, there are few methods for assessing the dispersing capacity of a lubricating composition against carbonaceous particulate. Currently, the only recognised method is the "Blotter Spot Test". The principle underlying this method can be summarised as follows:

1) a small amount of dispersion in the lubricant of polar carbonaceous particulate, or of used oil, is heated to 90° C.;
2) an aliquot (about 25 µl) is dripped on filter paper and allowed to incubate for 1 hour at 90° C.;
3) the filter paper is analysed obtaining a dispersion index calculated as the ratio of the diameter of the internal spot given by the insoluble carbonaceous residues to the diameter of the oil diffusion ring.

Figure 1:
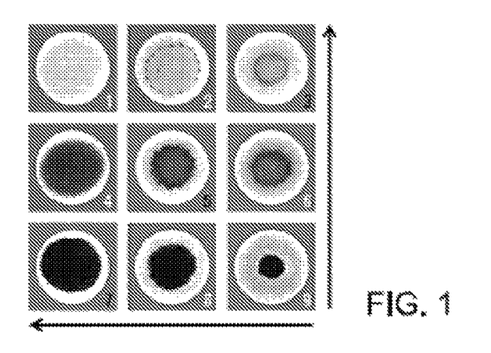
FIG. 1 schematically shows the results of a method for the assessment of the dispersing capacity of a lubricating composition in accordance with the prior technique called "Blotter Spot Test", carried out on lubricating compositions with different dispersing capacity.

FIG. 1 schematically shows 9 different spots which represent cases with different dispersion index. In particular, spot 1 is the one with the best dispersion index while spot 9 is the one with the worst dispersion index.

The "Blotter Spot Test" is therefore based on the quantification of the degree of dispersion observed on a spot of lubricant deposited on paper; therefore, the test result will depend on the type of paper, the method of deposition of the lubricant on the paper and the method of assessment of the dispersion index, which is generally subjective.

The "Blotter Spot Test" is a rather old method, which can be considered of a qualitative type as regards the defects mentioned above and which also does not have a high capacity of discriminating the dispersing properties of lubricants even with different characteristics.

Although softwares have recently been introduced that can analyse the spots deposited on paper by automatically providing the dispersion index, most of the limits mentioned above remain.

Ultimately, among the methods of the prior art for the assessment of the dispersing capacity of lubricating compositions and of additives, the engine tests are very expensive to conduct, requiring among other things large amounts of product to be tested, which makes them difficult to use, for example, for the preliminary assessment of various candidate compositions from which to select the one(s) with which to finalise the qualification of a new lubricant; the "Blotter Spot Test" laboratory method is not very reliable, due to the difficult reproducibility of the technique, the subjective assessment of the dispersion index and the low discrimination capacity of the dispersing properties of lubricants even with different characteristics.

Therefore, the need to have methodologies that allow a preliminary assessment of various lubricants and the selection of the most promising ones to be subjected to subsequent engine assessment remains.

SUMMARY OF THE DISCLOSURE

Therefore, aim of the present invention is to provide a method for the assessment of the dispersing capacity of new and used lubricating compositions (in particular for internal combustion engines) and of additives for lubricating compositions which is particularly simple to conduct even in a laboratory, without resorting to engine tests, and in any case effective and reliable.

In particular, aim of the invention is to provide an assessment method that allows the effective preliminary assessment of various lubricating compositions (or components thereof, for example additives) and the selection of the most promising ones to be subjected to subsequent engine assessment, with consequent optimisation of the cost of their development.

In accordance with these aims, the present invention relates to a method for the assessment of the dispersing capacity of new and used lubricating compositions (in particular for internal combustion engines) and of additives for lubricating compositions, as defined in the appended claim 1.

Preferred aspects and features of the invention are defined in the dependent claims.

The defects of the prior art are solved by the method in accordance with the invention, which achieves in particular the following advantages:

low cost and high speed of execution, as it is carried out in the laboratory using commonly used instruments;
high efficacy and reliability in the quantitative determination of the dispersing capacity of lubricating compositions;
high reproducibility and sensitivity.

Besides on the finished lubricating compositions, the method of the invention can also be effectively used for the determination, always with high effectiveness, reproducibility and sensitivity, of the dispersing power of additives for lubricants, such as dispersants and viscosity index improvers, and of partial lubricating compositions.

Furthermore, the method of the invention can also be used for the accurate assessment of the dispersing capacity of used lubricating compositions, that is, which have already been used in operation.

BRIEF DESCRIPTION OF THE DRAWINGS

The invention is further described in the following non-limiting example of embodiments, with reference also to the attached figures in which.

DETAILED DESCRIPTION OF THE DISCLOSURE

Basically, the method of the invention is characterized by the following main steps:
a) preparation of a dispersion of polar carbonaceous particulate in a composition to be tested (new or used lubricating composition or a fraction thereof, for example an additive to be used in a lubricating composition);
b) analysis of the aforesaid dispersion by optical microscopy with acquisition of images of the dispersion;
c) calculation of the degree of dispersion of the lubricating composition through analysis of the images acquired with a specific algorithm and assessment of the lacunarity, a parameter that measures the heterogeneity of the image and therefore is representative of the degree of dispersion.

If the method of the invention is applied to used lubricating compositions, it is not strictly necessary to prepare a dispersion on which to conduct the analysis, which can instead be conducted directly on the lubricating composition used as such, since the latter already contains dispersed carbonaceous particulate, generated during the use of the lubricating composition; alternatively, it is still possible to carry out the complete method by adding more carbonaceous particulate.

The main steps of the method of the invention are described in greater detail below.

a) Preparation of a carbonaceous particulate dispersion in the lubricating composition For the purposes of the invention, the amount of prepared dispersion can vary from 4 to 40 grams, preferably between 6 and 30 grams, while the container used for the preparation of said dispersion can be a glass container with a cap having a volume preferably between 30 and 60 ml.

It is understood that these indications (like the following ones) are provided purely by way of non-limiting example.

The procedure for preparing the dispersion is carried out through the following operations:

1) Preparation of a mixture containing the lubricating composition to be analysed/tested and an amount of carbonaceous particulate, expressed as a percentage by weight with respect to the total weight of the mixture, between 5% and 15%, preferably between 7% and 12%.

The mixture thus obtained is mixed at room temperature with an agitator (for example, an agitator produced by IKA, model VORTEX 3) operating at a speed between 1000 rpm and 1500 rpm, for a time between 2 minutes and 5 minutes.

For the preparation of the aforementioned mixture, carbonaceous particulates selected from the so-called commercially available Carbon Blacks can be used, characterized by a different size distribution of the primary unit and by a different surface polarity (i.e., amount of oxygen). A detailed description of the morphology and composition of various types of carbonaceous particulate is reported in the article "Multiscale Characterization of Some Commercial Carbon Blacks and Diesel Engine Soot" by G. Ferraro, E. Fratini, R. Rausa, P. Fiaschi, P. Baglioni, in Energy Fuels 2016, 30, 9859-9866.

Examples of carbonaceous particulates that can be used in the method of the present invention are: Vulcan XC72R, Corax N110, Corax N115, Corax N234, Corax N326, Corax N539, Corax N550 and Degussa S170.

Particularly preferred are Vulcan XC72R, Corax N110, Corax N115 and Corax N234 which can mimic different types of particulates that form in the engine, characterized by different oxygen content and sizes of the primary unit.

For example, Vulcan XC72R has a high polydispersity of the primary units with sizes between approximately 5 and 60 nm and high oxygen values (>5% by weight); on the other hand, Corax N110 has low oxygen values (<1.3% by weight) and primary units with low polydispersity with average sizes around 10 nm.

The other particulates, Corax N115 and Corax N234, on the other hand, have intermediate characteristics either in terms of oxygen content (i.e., polarity of the surface) or in terms of size distribution of the base unit.

In the method of the present invention, it is possible to use one of the carbonaceous particulates indicated above since with all of them it is possible to discriminate the dispersing capacity of the lubricating compositions subjected to the test, as demonstrated in the examples of the present patent application.

It is understood that the provided examples of suitable carbonaceous particulates are purely illustrative and other carbonaceous particulates may be employed as an alternative.

In general, it is convenient that the carbonaceous particulate employed in the method of the invention is a polar carbonaceous particulate.

Conveniently, the particulate used is characterized by a distribution of primary units (elementary particles not aggregated together) with a polar surface.

In particular, the carbonaceous particulate is a carbon black having:
- polydispersity (defined as the width at half height of the Gaussian distribution curves of the particle size) between about 10 nm and about 50 nm and preferably between about 20 nm and about 40 nm; and/or
- average sizes of the primary units between about 10 nm and about 70 nm, preferably between about 20 nm and about 50 nm; and/or
- surface polarity, i.e., amount of oxygen, between about 1% and about 9% and preferably between about 2% and about 6%.

On the other hand, it is not advisable to use real carbonaceous particulate, coming from exhausted lubricating compositions used in engine tests, since it presents various problems that make the use thereof in preparing dispersions suitable for the method of the invention difficult.

For example, the extraction and purification of the particulate from an exhausted lubricating composition is a particularly complex procedure that requires the use of centrifuges for the separation of the particulate from the matrix and/or extraction systems suitable for separating the particulate from the oily phase. In the A. D. H. Clague, J. B. Donnet, T. K. Wang, and J. C. M. Peng's publication "A comparison of diesel engine soot with carbon black", Carbon 37.10 (January 1999), 1553-1565, an example of separation of the particulate from an exhausted lubricant matrix by centrifugation and subsequent solvent extraction is reported, but it has been seen that this type of approach, in addition to producing limited amounts of particulate is not particularly reproducible as it leads to obtaining batches of particulates with variable characteristics. Furthermore, it should be pointed out that the nature of the particulates produced within a lubricating composition for engines can vary according to the type of engine used and also to the type of lubricant, even if it derives from the same engine. For all these reasons, it is preferable not to use the particulate extracted from real matrices of lubricating compositions as particulate model in the dispersion tests of the method of the invention, since it is not a particulate with reproducible characteristics.

2) The mixture obtained with the methods described under point 1) above is homogenized until a homogeneous paste is obtained.

By paste it is meant a dispersion of particulate in oil with a particulate concentration around 10% by weight, preferably between about 5% by weight and about 15% by weight, even more preferably between about 7% by weight and about 12% by weight.

For example, a homogenizer is used, in particular (but not necessarily) an Ultra-Turrax homogenizer (manufacturer IKA, model T25 digital) with S25N-8G head, operating at a number of revolutions between 18000 rpm and 24000 rpm, preferably between 20000 rpm and 21000 rpm, for a time exceeding 10 minutes, preferably for a time between 10 and 15 minutes, at a temperature between 60° C. and 90° C., preferably between 70° C. and 80° C.

Heating during homogenization is preferred as it leads to a certain decrease in the viscosity of the mixture and a more efficient homogenization.

3) Another amount of lubricating composition is added to the homogeneous paste obtained with the methods described under point 2) above in order to obtain a preliminary dispersion containing a concentration of carbonaceous particulate, expressed as a percentage by weight with respect to the total weight of the dispersion, between 0.5% and 7%, preferably between 1.5% and 5%.

The preliminary dispersion obtained is also homogenized with similar methods, for example, to those described under point 2), operating under the same operating conditions and with the same mixing time.

4) The preliminary dispersion obtained with the methods described under point 3) is allowed to equilibrate under mild stirring conditions; by mild stirring it is meant a stirring carried out with agitators operating at lower speeds (of at least one order of magnitude) than those of the previous homogenization steps and for a much longer time than the previous homogenization steps (several hours compared to a few minutes).

For example, an orbital thermo-agitator is used (manufacturer Torrey Pines Scientific, model ECHOTHERM SC20) operating at a number of revolutions between 200 and 500 rpm and at a temperature between 70° C. and 100° C., preferably between 80° C. and 90° C., for a time exceeding 24 hours. At the end of this operation, a final dispersion is obtained, ready to be analysed.

b) Analysis of dispersions by optical microscopy with acquisition of images of the dispersions The analysis, by optical microscopy, of the dispersions prepared in the previous step is carried out.

This type of analysis is carried out using an optical microscope equipped with a 10× objective (manufacturer Nikon, model Diaphot 300, equipped with CCD Nikon Digital Sight DS-5M-U1, light source: 50 W halogen bulb), keeping the sample at a temperature between 90° C. and 100° C., preferably at 100° C., with the aid of a heating stage with temperature control (manufacturer LINKAM, model PE94 Inverted Peltier Systems). The specimens for the analysis are prepared by depositing an amount between 2 and 6 µL, preferably between 3 and 5 µL, between two circular microscope slides with a thickness between 0.10 and 0.20 mm, preferably between 0.13 and 0.16 mm, and with a diameter between 20 and 50 mm, preferably between 30 and 40 mm.

Figure 2:
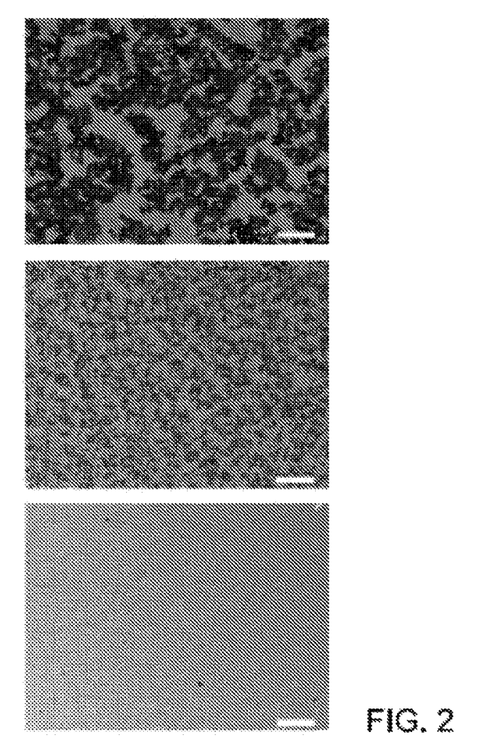
FIG. 2 shows, by way of example, three optical micrographs acquired on three different samples prepared in accordance with the method of the invention and having different degree of dispersion of carbonaceous particulate.

FIG. 2 shows, by way of example, the optical micrographs acquired on three different samples with different degree of dispersion.

c) Calculation of the degree of dispersion of the lubricating compositions

An image descriptor is used to calculate the degree of dispersion.

In particular, in accordance with the invention the selected image descriptor is the lacunarity (A).

The lacunarity is a measure of how a spatial pattern fills the space, where a pattern with more and/or larger gaps (empty spaces) has a larger lacunarity.

The lacunarity, in addition to providing an indication of the degree of occupied space, also quantifies additional characteristics of a pattern such as rotational or roto-translational invariance and, more generally, heterogeneity.

For example, a low-lacunarity pattern, if rotated by 90°, substantially does not change as it is highly homogeneous, whereas a more heterogeneous (with high lacunarity) pattern changes significantly.

The lacunarity is therefore essentially a measure of the roto-translational heterogeneity or invariance of an image.

By simply describing the procedure for calculating this parameter, a grid is created on the image to be treated (FIG. 3) and the pixel density in each cell (or box) of the grid is evaluated as the size of the grid and the orientation of the latter varies with respect to a reference system.

Figure 3:
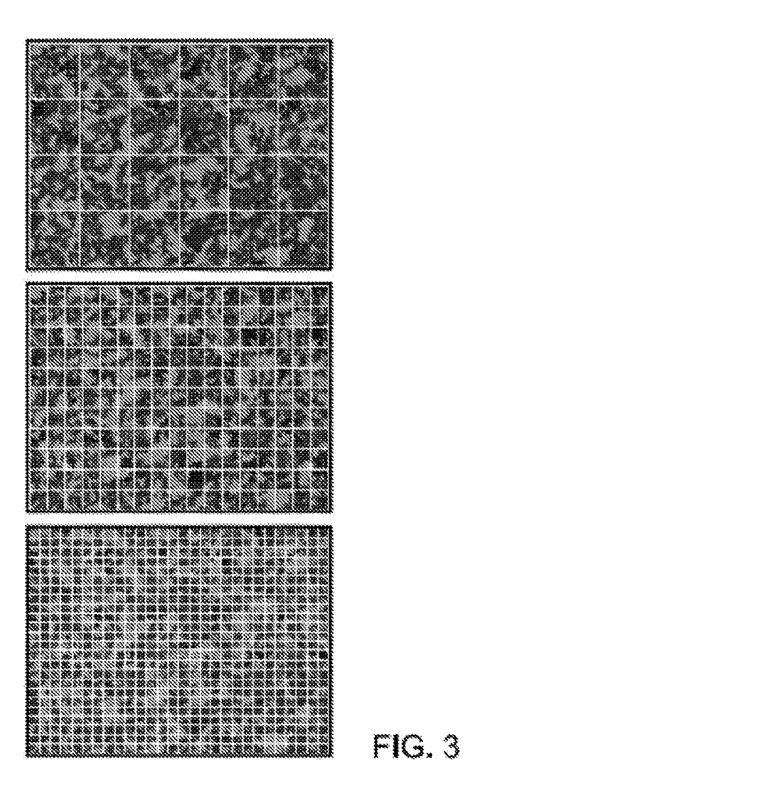
FIG. 3 shows three examples of grids constructed in accordance with the method of the invention for measuring the lacunarity in the images represented in the respective micrographs.

The formula used to calculate the lacunarity is as follows:

$$\lambda_{\varepsilon,g} = \left(\frac{\sigma}{\mu}\right)^2_{\varepsilon,g} \quad (I)$$

where:
μ is the average of pixels per cell at each ε,
ε is the scale applied to the image (ε=ratio between cell size and image size),
g is the orientation of the grid with respect to the image,
σ is the standard deviation.

The final lacunarity value (Λ) will be that obtained by averaging all the possible orientations of the grid (Ng):

$$\Lambda = \frac{\sum \lambda_g}{N_g} \quad (II)$$

A complete definition and in-depth discussion of the lacunarity is reported in the literature, for example in Karperien, A., "FracLac for ImageJ", 1999-2013:
http://rsb.info.nih.gov/ij/plugins/fraclac/FLHelp/Introduction.htm One of the big advantages of using the lacunarity as an image descriptor is that the lacunarity can be used directly on an 8-bit grayscale image.

In this way, once the image has been obtained from a microscope, it is sufficient to calculate the lacunarity without previously treating the image.

The lacunarity value obtained will depend solely on the scale applied to the image and the number of grid orientations chosen.

Therefore, lacunarities calculated on different images, acquired with the same resolution, using the same parameters for the calculation will be directly comparable, i.e., the quantification of the degree of dispersion becomes univocal and reproducible in any laboratory.

The calculation of the lacunarity is carried out by means of an algorithm that can be implemented by a program (software).

An example of a program available is the FracLac open-source software which can be used as a plug-in for ImageJ.

In general, the calculation algorithm comprises the operations of:
acquiring the micrographic image (through optical micrograph);
dividing the image into separate and non-overlapping cells of a grid;
calculating the lacunarity using the formulas mentioned above.

EXAMPLES

In order to better understand the present invention, some illustrative and non-limiting examples are reported below.

By way of example, reference lubricating compositions of the DV4 (CEC-L-93-04) and DV6 (CEC-L106-16) engine tests were used in the method of the invention. In particular, two reference lubricating compositions are used in each of said engine tests:
"Positive Reference", a lubricating composition having a good dispersing capacity and which therefore in the corresponding engine test produces a low viscosity increase, at a given concentration value of particulate present;
"Negative Reference", a lubricating composition which have worse dispersing capacities than the previous one and which therefore in the engine test produces a higher viscosity increase, with the same concentration of particulate present.

The lubricating compositions (hereinafter also referred to briefly as "formulation") whose dispersing capacity has been assessed in examples 1-24 described herein are as follows:
A: "high reference" for DV4 engine test (CEC code: RL 216)
B: "low reference" for DV4 engine test (CEC code: RL 223)
C: "high reference" for DV6 engine test (CEC code: RL 247)
D: "low reference" for DV6 engine test (CEC code: RL 248)

The comparative examples 1 to 8 do not relate to the method of the invention, since they all use a different procedure for preparing the carbonaceous particulate dispersion.

In particular, examples 1-4 use the Blotter Spot Test as an analytical method for the assessment of the dispersions while examples 5-8 use optical micrograph.

The Examples 9 to 24, on the other hand, relate to the method of the invention, either as regards the preparation of the particulate dispersion, or as regards the analytical method for the assessment of the dispersions.

The aim of these examples is to show that the method of the invention is effectively capable of discriminating the dispersing capacities of the lubricating compositions placing them in the same order detected by the motor tests.

Comparative Examples 1-8

Dispersions were prepared in ways different from those of the invention.

The procedure used to prepare the carbonaceous particulate dispersions in the lubricating compositions is as follows:
1) Preparation of a mixture containing the lubricating composition and an amount of Vulcan XC72R carbonaceous particulate, expressed as a percentage by weight with respect to the total weight of the mixture, equal to 28. The mixture thus obtained is mixed at room temperature with an agitator (manufacturer IKA, model VORTEX3) operating at 1500 rpm, for a time of 2 minutes.
2) The mixture obtained under point 1) is homogenized by letting it sonicate for about 30 minutes with a sonicator in a bath at 40 kHz, at the power of 100% and at a temperature of 25° C.
3) The dispersion thus obtained is allowed to equilibrate for a time of 28 hours in an orbital thermo-agitator (manufacturer Torrey Pines Scientific, model ECHO-THERM SC20) operating at a number of revolutions of 350 rpm and at a temperature of 70° C. At the end of this operation, the final dispersion is obtained, ready to be analysed.

The Examples of dispersions prepared with this method are as follows:
Examples 1 and 5: formulation A and dispersion method not according to the invention;
Examples 2 and 6: formulation B and dispersion method not according to the invention;
Examples 3 and 7: formulation C and dispersion method not according to the invention;
Examples 4 and 8: formulation D and dispersion method not according to the invention.

The dispersions prepared in accordance with the method described above (not in accordance with the invention) were tested with the Blotter Spot Test (examples 1 to 4) and with optical micrograph (examples 5 to 8).

Below are the results obtained with the Blotter Spot test.

The procedure followed to carry out this type of test has been optimised starting from what is present in the literature and can be briefly summarized as follows:

1) a small aliquot of the prepared dispersion is heated to 90° C. for 20 minutes;
2) about 10 μL of this dispersion are deposited on filter paper and the spot is allowed to develop for about 1 hour at 90° C.;
3) the spot obtained is analysed in terms of size, shades of grey and homogeneity.

Figure 4A:
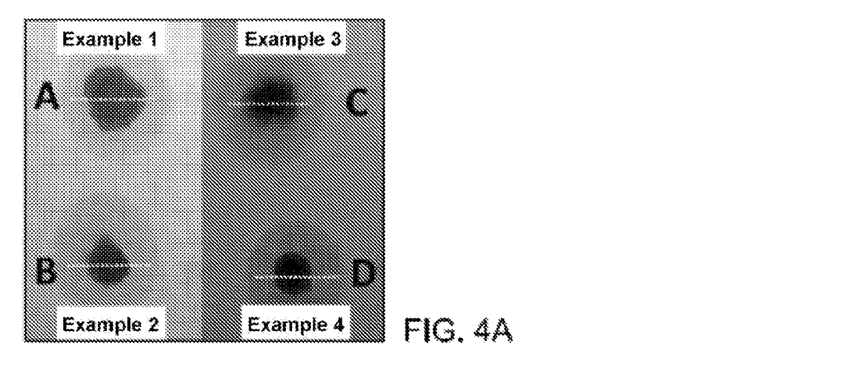
FIG. 4A and FIG. 4B report the results of Blotter Spot Test carried out on four dispersions prepared not following the method of the invention and the relative diffusion profiles expressed in grayscale.

In particular, the greater the degree of dispersion of the particulate in the organic phase, the more homogeneous and the wider the spot of diffusion of the dispersion will be. FIG. 4A shows the Blotter Spot Tests performed on all four dispersions prepared in Examples 1-4 and FIG. 4B the relative diffusion profiles expressed in grayscale.

Figure 4B:
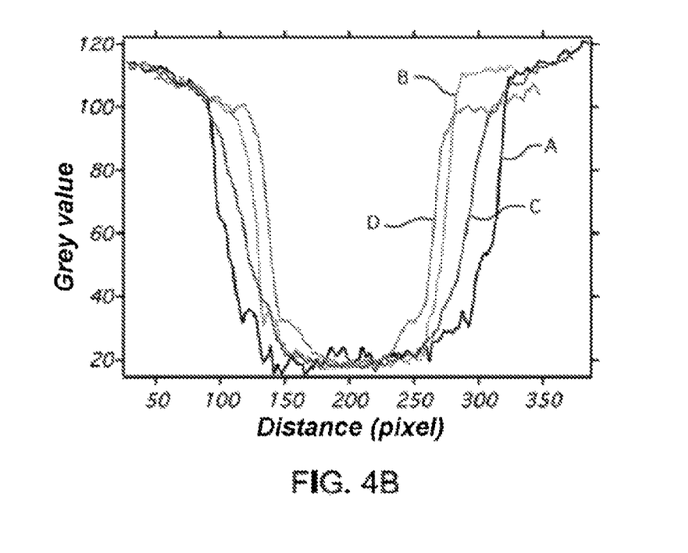

The results obtained from this test are difficult to interpret. In particular, it seems that only the system containing the formulation A gives a wider diffusion spot (example 1) while the spots of the other examples seem more or less comparable especially if the grey profiles are analysed with different orientations of the spot. The Blotter Spot Test therefore proved inadequate as it failed to discriminate the dispersing capacity of the various compositions.

The results obtained on the aforementioned dispersions using optical microscopy are reported below (examples 5 to 8). This type of analysis is carried out with an optical microscope equipped with a 10× objective (manufacturer Nikon, model Diaphot 300, equipped with CCD Nikon Digital Sight DS-5M-U1, light source: 50 W halogen bulb), keeping the sample at a temperature of 100° C., with the aid of a heating stage with temperature control (manufacturer LINKAM, model PE94 Inverted Peltier Systems).

The specimens for the analysis are prepared by depositing 5 μL of dispersion between two circular microscope slides with a thickness between 0.10 and 0.20 mm and with a diameter of 30 mm.

Figure 5:
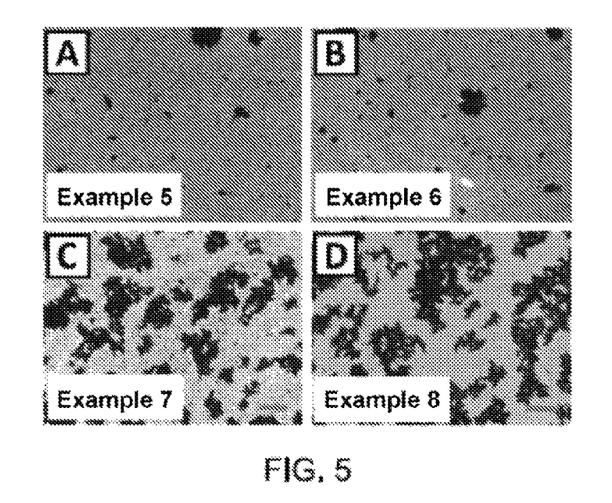
FIG. 5 shows four optical micrographs acquired on respective samples prepared not in accordance with the method of the invention and having different degree of dispersion of carbonaceous particulate.

FIG. 5 shows the optical micrographs relative to the dispersions of the examples 5, 6, 7 and 8, prepared with the formulations A, B, C and D. From these micrographs it is possible to directly compare the dispersing power of the different systems as they contain the same amount of carbonaceous particulate and lubricating composition.

From the optical micrographs of FIG. 5 it seemingly emerge that the formulations A and B have the same dispersing capacity as the carbonaceous particulate, like the formulations C and D with respect to each other; the formulations C and D have a worse dispersing capacity than the formulations A and B.

However, these results do not reflect the real performance of the formulations (which are reference formulations whose properties are fully defined and known).

In conclusion, the results obtained either with the Blotter Spot Test or with the Optical Micrograph using the above particulate dispersion procedure are not in line with the known properties of the reference lubricating compositions. In particular, it should be noted that the Blotter Spot Test is not able to discriminate the dispersing capacity of the various compositions.

Examples 9-24

Various lubricating compositions have been prepared following the method of the invention.

In particular, the same reference lubricating compositions A, B, C, D used also in the comparative examples described above were used, but in this case following the method of the invention either for the preparation of the carbonaceous particulate dispersions or for the assessment of the degree of dispersion of the particulate.

The dispersions were prepared, for all the reference lubricating compositions, using 2.7% by weight of different types of carbonaceous particulate.

The tests with the different types of particulates were conducted in order to verify whether the nature of them substantially affects the result obtained.

In particular, different commercial carbon blacks with different size distribution of the primary unit and different surface polarity (i.e., amount of oxygen) were tested.

In the Examples 9-12, Vulcan XC72R particulate was used, which is characterized by a wide distribution of primary units (diameter between 5 and 80 nm) and high oxygen levels (5.7%).

In the Examples 13-16, Corax N110 particulate was used, which is characterized by a narrow distribution of primary units (diameter between 5 and 25 nm) and low oxygen levels (1.3%).

In the Examples 17-20, Corax N115 particulate was used, which is characterized by a relatively wide distribution of primary units (diameter between 5 and 50 nm) and high oxygen levels (5.8%).

In the Examples 21-24, Corax N234 particulate was used, which is characterized by a narrow distribution of primary units (diameter between 5 and 40 nm) and high oxygen levels, comparable to Vulcan XC72R (5.7%).

The procedure for preparing the dispersions was carried out in accordance with the method of the invention, as follows:

1) Preparation of a mixture containing the lubricating composition and an amount of carbonaceous particulate, expressed as a percentage by weight with respect to the total weight of the mixture, of 10%. The mixture thus obtained was mixed with an agitator (manufacturer IKA, model VORTEX3) operating at 1500 rpm for a time of 10 minutes.
2) The mixture obtained under point 1) was homogenized with Ultra-Turrax IKA homogenizer, model T25 digital, with S25N-8G head, operating at a number of revolutions of 20000 rpm, for a time of 15 minutes, at a temperature of 75° C. At the end of this operation, a homogeneous paste was obtained.
3) An amount of a base oil was added to the paste obtained under point 2), so as to obtain a dispersion containing a concentration of carbonaceous particulate of 2.7% by weight with an oil phase composed of about 75% by weight of lubricating formulation to be tested and 25% by weight of base oil.

ENI SN150 base oil was used as base oil.

The addition or not of base oil, such as for example ENI SN150 base oil, depends on the dispersing capacity of the formulation to be investigated.

Low-performing formulations, that is, which have reduced dispersing capacities, can be tested and investigated even pure, i.e., without dilution with base oil.

On the other hand, in the case of formulations with better dispersing capacities, the oil/particulate system may appear dispersed already at particulate concentrations around 7% by weight. On the other hand, further increasing the amount of particulate would make the slide unreadable as it is too much loaded with carbonaceous material. In these cases, it may therefore be appropriate to add base oil, diluting the formulation in a known amount of base oil (i.e., a lubricating composition with known properties) before the study. The base oil therefore serves as a continuous inert phase to make the slide optically legible.

The obtained dispersion was homogenized as under point 2), operating under the same operating conditions and with the same mixing time.

4) The dispersion obtained under point 3) was allowed to equilibrate for a time of 28 hours in an orbital thermo-agitator (manufacturer Torrey Pines Scientific, model ECHOTHERM SC20) operating at a number of revolutions of 300 rpm and at a temperature of 75° C. At the end of this operation, a final dispersion was obtained, ready to be analysed.

Figure 6:
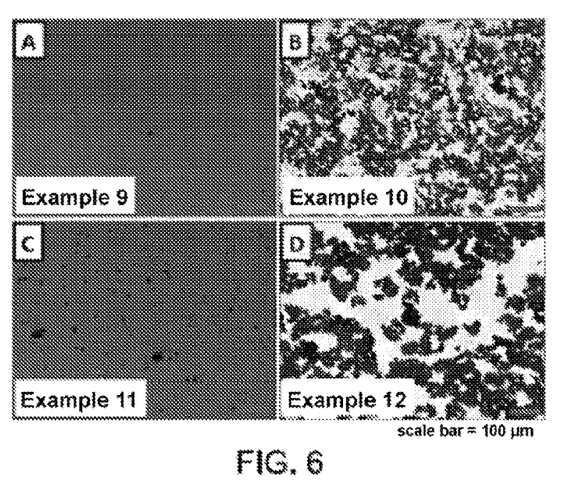
FIG. 6 shows four optical micrographs acquired on respective samples prepared in accordance with the method of the invention and having different degree of dispersion of a first type of carbonaceous particulate.

FIG. 6 shows the optical micrographs of the dispersions (examples 9-12) containing Vulcan XC72R particulate in the four reference lubricating compositions A, B, C, D.

As already highlighted, the Vulcan XC72R particulate is characterized by a wide distribution of primary units (diameter between 5 and 80 nm) and high oxygen levels (5.7%).

From the images it is evident that the lubricating compositions B and D produce the most aggregated dispersions compared to those produced with the lubricating compositions A and C. The lacunarity of the image was determined ($\varepsilon(max)=4$ pixels, $g=9$) to quantify the degree of aggregation.

Figure 7:
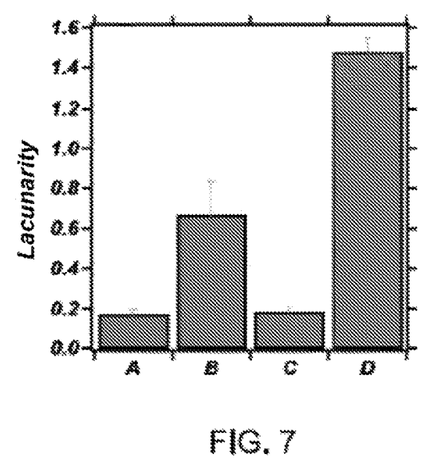
FIG. 7 is a histogram showing the lacunarities calculated on the optical micrographs of FIG. 6.

FIG. 7 shows the histogram with the lacunarities calculated on the optical micrographs acquired on the different dispersions.

The lacunarity results confirm that the lubricating compositions A and C give rise to micrographs with less lacunarity (i.e., more dispersed) while the lubricating compositions B and D give rise to more aggregated dispersions. These results are perfectly consistent with the known properties of the reference lubricating compositions.

Furthermore, the differences between the morphologies of the dispersions prepared with the lubricating compositions B and D can be highlighted. The morphology of the dispersion prepared with the lubricating composition B has a lower lacunarity value than that prepared with the lubricating composition D.

Figure 8:
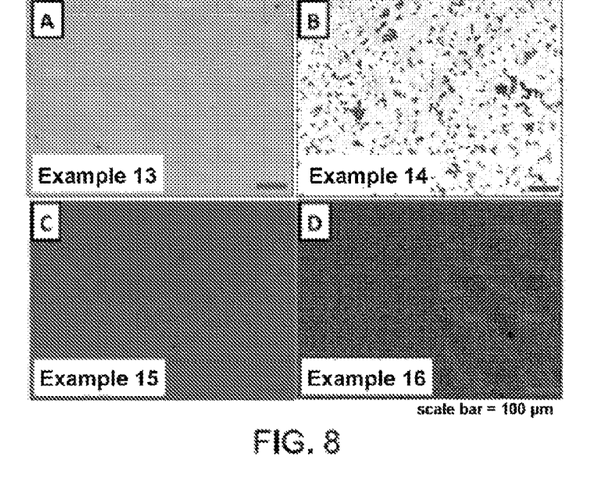
FIG. 8 shows four optical micrographs acquired on respective samples prepared in accordance with the method of the invention and having different degree of dispersion of a second type of carbonaceous particulate.

FIG. 8 shows the optical micrographs of the dispersions (examples 13-16) prepared by dispersing the Corax N110 particulate in the four reference lubricating compositions A, B, C, D.

As already highlighted, the Corax N110 particulate is characterized by a narrow distribution of primary units (diameter between 5 and 25 nm) and low oxygen levels (1.3%).

As can be noted from the micrographs, all four lubricating compositions give rise to dispersed systems. Despite the high degree of dispersion reached with such particulate concentrations, it is possible to note how the lubricating compositions B and D produce more aggregated dispersions than those produced with the lubricating compositions A and C and therefore in line with the known properties of the reference lubricating compositions.

Like in the previous examples, the lacunarity of the image was determined ($\varepsilon(max)=4$ pixels, $g=9$) to quantify the degree of aggregation.

Figure 9:
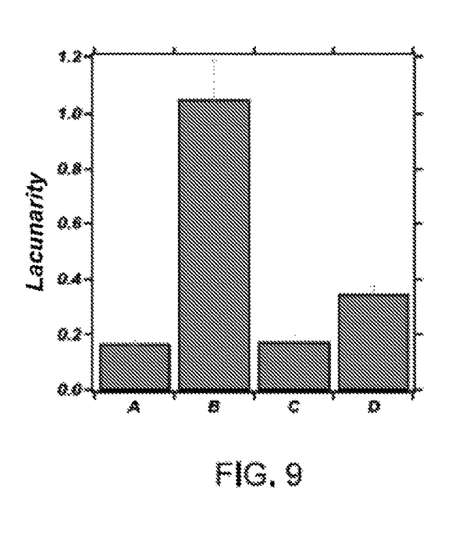
FIG. 9 is a histogram showing the lacunarities calculated on the optical micrographs of FIG. 8.

FIG. 9 shows the histogram with the lacunarities calculated on the optical micrographs acquired on the different dispersions.

Figure 10:
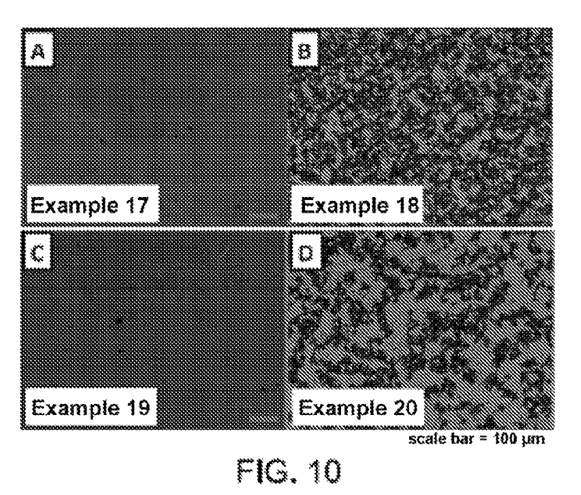
FIG. 10 shows four optical micrographs acquired on respective samples prepared in accordance with the method of the invention and having different degree of dispersion of a third type of carbonaceous particulate.

FIG. 10 shows the optical micrographs of the dispersions (examples 17-20) prepared by dispersing the Corax N115 particulate in the four reference lubricating compositions A, B, C, D.

As already highlighted, the Corax N115 particulate is characterized by a distribution of primary units between 5 and 50 nm and high oxygen levels (5.8%).

As can be seen from the micrographs, the lubricating compositions B and D produce more aggregated dispersions than those produced with the lubricating compositions A and C.

Like in the previous case, the lacunarity of the image was determined ($\varepsilon(max)=4$ pixels, $g=9$) to quantify the degree of aggregation.

Figure 11:
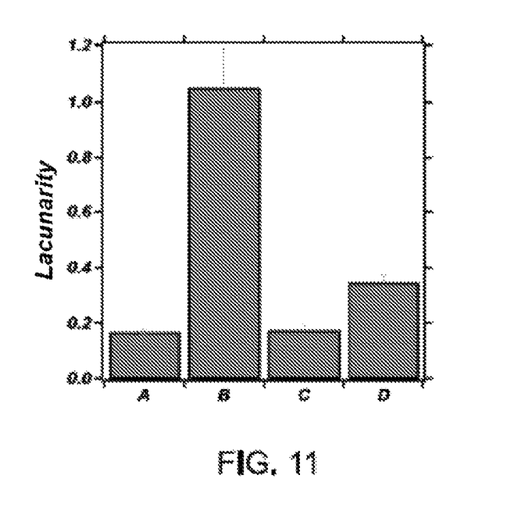
FIG. 11 is a histogram showing the lacunarities calculated on the optical micrographs of FIG. 10.

FIG. 11 shows the histogram with the lacunarities calculated on the optical micrographs acquired on the different dispersions.

The lacunarity results confirm that the lubricating compositions A and C give rise to micrographs with less lacunarity (i.e., more dispersed) while the lubricating compositions B and D give rise to more aggregated dispersions. The results are therefore in line with the known properties of the reference lubricating compositions.

Figure 12:
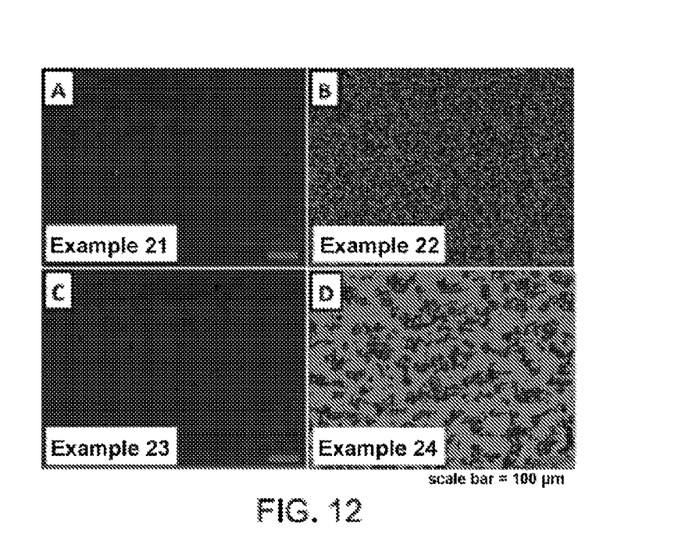
FIG. 12 shows four optical micrographs acquired on respective samples prepared in accordance with the method of the invention and having different degree of dispersion of a fourth type of carbonaceous particulate.

FIG. 12 shows the optical micrographs of the dispersions (examples 21-24) prepared by dispersing the Corax N234 particulate in the four reference lubricating compositions A, B, C, D.

As already highlighted, the Corax N234 particulate is characterized by a narrow distribution of primary units (diameter between 5 and 40 nm) and oxygen levels comparable to Vulcan XC72R (5.7%).

From the optical micrographs it is possible to note how the lubricating compositions B and D produce more aggregated dispersions than those produced with the lubricating compositions A and C.

Like in the previous case, the degree of aggregation was quantified through the lacunarity of the image ($\varepsilon(max)=4$ pixels, $g=9$).

Figure 13:
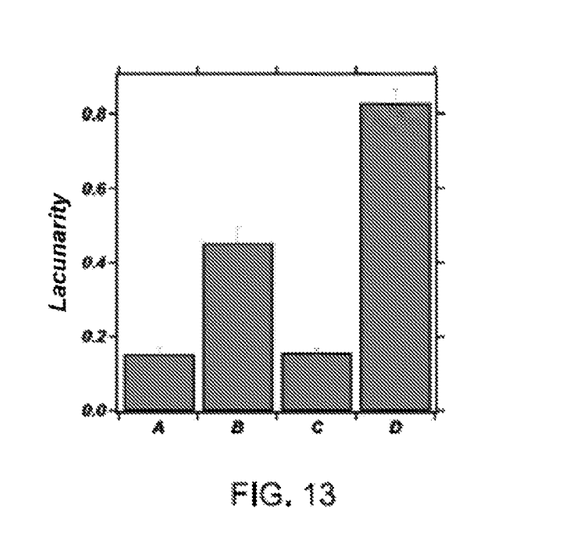
FIG. 13 is a histogram showing the lacunarity calculated on the optical micrographs of FIG. 12.

FIG. 13 shows the histogram with the lacunarities calculated on the optical micrographs acquired on the different dispersions.

The lacunarity results obtained confirm, also in this case, that the lubricating compositions A and C give rise to micrographs with less lacunarity (i.e., more dispersed) while the lubricating compositions B and D give rise to more aggregated dispersions.

The method of the invention has therefore been confirmed to be capable of determining the dispersing capacity of the four reference lubricating compositions, in accordance with their characteristics and in particular highlighting that the lubricating compositions A and C are those which have a better dispersing capacity since they better contrast particulate aggregation (i.e. low lacunarity values) while the lubricating compositions B and D are those that give rise to more aggregated (i.e. high lacunarity values) and less dispersed systems.

All four carbonaceous particulates used, having rather different characteristics, discriminated the dispersing capacity of the four reference lubricating compositions.

Therefore, the experimental results confirm that the method subject-matter of the present invention provides excellent results and can be used for selecting among various candidate lubricating compositions the one or those with which to continue the qualification by carrying out the engine tests envisaged.

More Examples

Further examples have been carried out by varying the operating conditions of the various steps of the method of the invention within the limits indicated above.

In particular, further experimental tests were carried out, as well as with other lubricating compositions and fractions or components (additives) of lubricating compositions, varying one or more between:
- amount of carbonaceous particulate in the analysed dispersion;
- type of carbonaceous particulate used;
- operating conditions of the steps of preparation of the initial mixture, of the preliminary dispersion, of the final homogeneous dispersion; and/or the steps of homogenization of the paste and/or of the preliminary dispersion;
- amount of dispersion deposited on the observation support;
- possible dilution in base oil.

In all cases, the effectiveness of the method of the invention was confirmed in the assessment of the dispersing capacity of new and used lubricating compositions (in particular for internal combustion engines) and of additives for lubricating compositions.

The invention claimed is:

1. A method for the assessment of the dispersing capacity of new or used lubricating compositions and/or of additives for lubricating compositions, the method comprising the steps of:
   providing a homogeneous dispersion of at least one carbonaceous particulate in a composition to be tested, the homogeneous dispersion consisting of a lubricating composition or a fraction or component thereof;
   acquiring at least one micrographic image of a sample of the homogeneous dispersion, deposited on an observation support; and
   calculating a lacunarity of the acquired image as a parameter representative of a degree of dispersion of the carbonaceous particulate in the composition.

2. The method according to claim 1, wherein the step of calculating the lacunarity comprises the steps of:
   defining, on the image, a grid formed by a plurality of cells;
   evaluating a pixel density in each cell of the grid according to grid size and grid orientation with respect to a fixed reference system;
   calculating the lacunarity with formula (I):

$$\lambda_{\varepsilon,g} = \left(\frac{\sigma}{\mu}\right)^2_{\varepsilon,g} \quad (I)$$

wherein:
$\mu$ is the average of pixels per cell at each $\varepsilon$,
$\varepsilon$ is the scale applied to the image,
g is the orientation of the grid with respect to the image,
$\sigma$ is the standard deviation;
calculating a final lacunarity ($\Lambda$) as an average over all possible grid orientations (Ng), with formula (II):

$$\Lambda = \frac{\sum \lambda_g}{N_g}. \quad (II)$$

3. The method according to claim 1, wherein the carbonaceous particulate is a carbon black selected from the group consisting of: Vulcan XC72R, Corax N110, Corax N115, Corax N234, Corax N326, Corax N539, Corax N550 and Degussa S170.

4. Method according to claim 1, wherein the step of acquiring the image is carried out with an optical microscope equipped with an objective at least 10×, keeping the sample at a temperature of at least 80° C.

5. The method according to claim 1, wherein the sample is maintained during the step of acquiring the optical micrographic image at a temperature from 90° C. to 100° C.

6. The method according to claim 1, wherein the homogeneous dispersion sample is prepared by depositing a quantity between 2 and 6 µL between two microscope slides.

7. The method according to claim 1, wherein the carbonaceous particulate in the mixture is in an amount between 5% and 15% of the total weight of the mixture.

8. The method according to claim 7, wherein the amount of carbonaceous particulate in the mixture is between 7% and 12%.

9. The method according to claim 1, wherein the preliminary dispersion contains a concentration of carbonaceous particulate expressed as a percentage by weight of the total weight of the dispersion that is between 0.5% and 7%.

10. The method according to claim 9, wherein the preliminary dispersion contains a concentration of carbonaceous particulate between 1.5% and 5%.

11. The method according to claim 1, wherein the carbonaceous particulate is a carbon black having a polydispersity, defined as the width at mid-height of the Gaussian particle size distribution curves, between 10 nm and 50 nm and/or an average particle sizes between 10 nm and 70 nm and/or a surface polarity between 1% and 9%.

12. The method according to claim 11, wherein the polydispersity is between 20 nm and 40 nm; and/or the average particle sizes is between 20 nm and 50 nm; and/or the surface polarity is between 2% and 6%.

13. The method according to claim 1, wherein the step of providing the homogeneous dispersion comprises the steps of:
   preparing a mixture comprising a predetermined amount of carbonaceous particulate and a first amount of lubricating composition or a fraction or component thereof;
   homogenizing the mixture until a homogeneous paste is obtained;
   adding a second amount of lubricating composition to the paste se as to obtain a preliminary dispersion;
   homogenizing the preliminary dispersion; and
   equilibrating the preliminary dispersion under mild stirring conditions and forming the homogeneous dispersion.

14. The Method according to claim 13, wherein the mixture is mixed at a room temperature with a mixer operating at a speed between 1000 rpm and 1500 rpm for a time between 2 minutes and 5 minutes.

15. The method according to claim 13, wherein the step of equilibrating the preliminary dispersion is conducted with a thermo-agitator operating at a speed between 200 and 500 rpm and at a temperature between 70° C. and 100° C. for a time exceeding 24 hours.

16. The method according to claim 15, wherein the thermo-agitator is an orbital thermo-agitator.

17. The method according to claim 13, wherein the homogenizing the mixture and the homogenizing the preliminary dispersion are carried out with a homogenizer operating at a speed between 18000 rpm and 24000 rpm, for a time exceeding 10 minutes at a temperature between 60° C. and 90° C.

18. The method according to claim 17, wherein the temperature is between 70° C. and 80° C.

19. The method according to claim 17, wherein the speed is between 20000 rpm and 21000 rpm.

20. The method according to claim 17, wherein the time is between 10 and 15 minutes.

* * * * *